United States Patent [19]

Olson

[11] Patent Number: 4,708,148

[45] Date of Patent: Nov. 24, 1987

[54] MEASUREMENT OF SPINE EXTENSION

[75] Inventor: Gary M. Olson, Ashville, N.Y.

[73] Assignee: Ganebac, Inc., Ashville, N.Y.

[21] Appl. No.: 784,749

[22] Filed: Oct. 7, 1985

[51] Int. Cl.⁴ .............................................. A61B 5/10
[52] U.S. Cl. ................... 128/781; 128/782; 33/512
[58] Field of Search ............... 128/774, 781–782; 33/511–512, 515

[56] References Cited

U.S. PATENT DOCUMENTS

| | | | |
|---|---|---|---|
| 4,036,213 | 7/1977 | Gregory | 128/781 |
| 4,108,164 | 8/1978 | Hall, Sr. | 128/781 |
| 4,285,515 | 8/1981 | Gezari | 128/774 X |
| 4,425,713 | 1/1984 | Rotella | 128/774 X |
| 4,492,236 | 1/1985 | Pile | 128/781 |

FOREIGN PATENT DOCUMENTS 7435361  6/1976  France .................. 128/781

Primary Examiner—William E. Kamm
Assistant Examiner—Angela D. Sykes
Attorney, Agent, or Firm—Larson and Taylor

[57] ABSTRACT

An apparatus and method for measuring the end range extension of the lumbar spine of a standing patient is disclosed. A brace device is provided for movably bracing the sacroiliac of the patient against backward movement and a hip holding device is also provided for holding the hips of the patient in contact with the brace device. A measuring device then measures the backward displacement of identifiable portion of the upper body of the patient to determine the end range extension. Preferably, a device is also provided for holding the feet of the patient against upward movement and to hold the feet directly below the hips. The knees are also preferably held in a locked position. The measuring device is adjustable to fit each individual patient appropriately.

17 Claims, 3 Drawing Figures

MEASUREMENT OF SPINE EXTENSION

FIELD OF THE INVENTION

The present invention relates generally to the measurement of the extension of the spine, and more particularly to the exact measurement of the end range extension of the lumbar spine at the xiphoid process.

BACKGROUND OF THE INVENTION

The impact of non-specific low back pain is very significant. There are a multitude of factors which are beginning to be identified as contributing to the cause of low back pain. It is a well documented fact that back problems are one of the most costly elements at this time.

The majority of patients with back pain do not display clinical symptoms. Rather, their pain is related to non-specific or mechanical causes. The identification of work place and individual risk factors, including the development of appropriate preventive programs is an acknowledged need. Contemporary viewpoints concerning treatments are shifting from the traditional medical model of care to preventive and maintainance oriented programs organized and run at the work site. Understandably, this new emphasis has led to the need to develop more sensitive evaluation tools.

The loss of ability to freely extend the lumbar spine has been cited by numerous investigators as being associated with non-specific low back pain. Thus, there is a need for a definitive biomedical dependent measure to quantify this observed association.

Disclosed in U.S. Pat. No. 4,485,825 (Domjan et al) is an instrument for measuring displacements of joints and the spinal column. The instrument consists of a combination of a dip-circle (inclinometer) and a compass which are used to measure vertical and horizontal displacements, respectively. Measurements of the spine can be made by using four of these devices attached a various locations along the spine.

Another method of measuring the end range extension of the lumbar spine is known as the Cureton test. This test was designed to measure the flexibility of athletes. According to the method, the subject first lies prone on a table with his feet held down and his hips in firm contact with the table. The subject next raises his trunk as far backward as possible. The Examiner then measures the vertical distance from the suprasternale to the top of the table. This measurement is then multiplied by 100, and the product divided by the trunk length. The measurement of trunk length is made with the subject seated on a bench with his back flat against a wall. The vertical distance between the suprasternale and the bench is then determined. During this measurement, the subject is instructed not to make any effort to raise his chest, but merely to direct his head up moderately.

Other general devices in the prior art for measuring bone structure or body measurements of a patient have been disclosed. Example of these devices are disclosed in U.S. Pat. No. 3,575,159 (Pile et al) and U.S. Pat. No. 4,135,498 (McGee).

Although there is now a recognized need to provide a measurement of the end range extension of the lumbar spine, none of the above devices disclosed in the prior art provide a simple and efficient measurement of this extension which is easily read and easily repeated.

SUMMARY OF THE INVENTION

In accordance with the present invention, an apparatus and method for measuring the end range extension of the lumbar spine of a standing patient is disclosed. In order to make this measurement, a brace means is provided for immovably bracing the sacroiliac of the patient against backward movement. A hip holding means is then provided for holding the hip of the patient in contact with this brace means. Finally, a measuring means for measuring the backward displacement of an identified portion of the upper body of the patient is used to effect the measurement.

In a preferred embodiment of the present invention, a foot holding means is provided for holding the feet of the patient against upward movement and also to hold the feet directly below the hips. In addition, a knee holding means is provided for holding the knees of patient in a locked position. Conveniently, a base is also provided to which the brace means, hip holding means, measuring means, foot holding means, and knee holding means are all attached.

According to the present invention, the displacement measurement of the extension of the lumbar spine is measured at the xiphoid process of the patient. In addition, the brace means, hip holding means, and knee holding means are made adjustable to suit the needs of each individual patient. The measuring means is also made adjustable in order to measure horizontally along a horizontal bar which is adjustable vertically to the level of the xiphoid process of the patient. This horizontal bar is also slidable horizontally toward and away from the patient and provides a zero point for the xiphoid process of the patient before bending backward.

In the preferred embodiment, the foot holding means includes a toe bar located above the feet of the user. This toe bar is mounted on a horizontal slide means and is adjustable therealong to fit each patient.

It is an advantage of the present invention that a simple and easily performed measurement of the end range extension of the lumbar spine is performed.

It is also an advantage of the present invention that the apparatus used is adjustable to fit each individual being measured.

It is a further advantage of the present invention that the measuring can be performed by relatively untrained operators.

Other features and advantages of the present invention are stated in or apparent from a detailed description of a presently preferred embodiment of the invention found hereinbelow.

DETAILED DESCRIPTION OF THE PREFERRED EMBODIMENT

Figure 1:
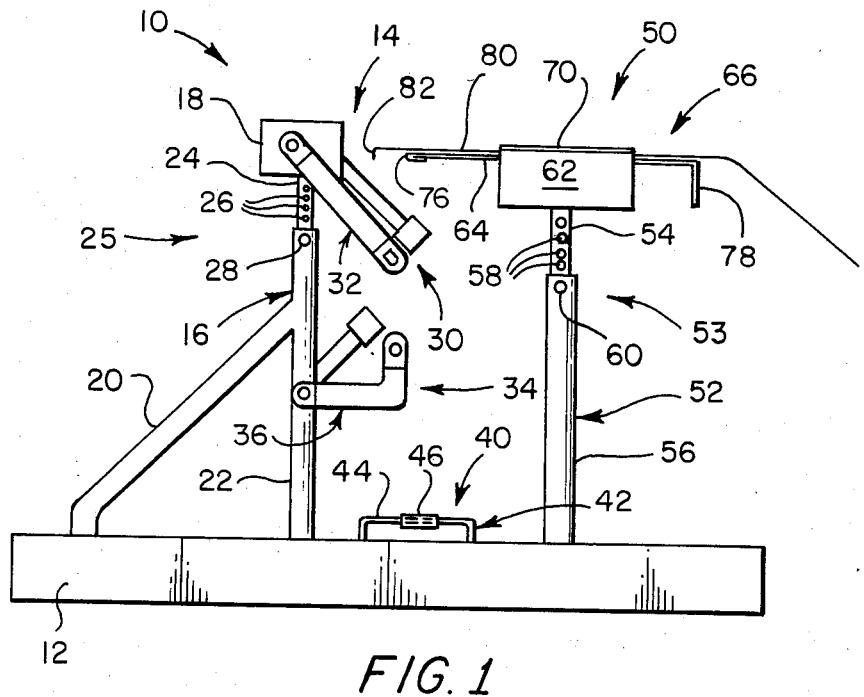
FIG. 1 is a side elevation view of the apparatus for measuring the end range extension of the lumbar spine according to the present invention.
Figure 2:
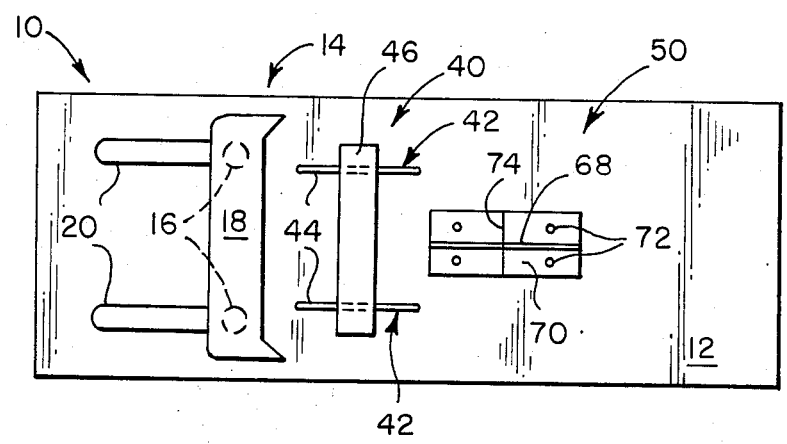
FIG. 2 is a top plane view of the apparatus depicted in FIG. 1.

With reference now to the drawings in which like numerals represent like elements in the two drawings, a measuring device 10 for measuring the end range extension of the lumbar spine of a standing patient is depicted in FIGS. 1 and 2. Measuring device 10 includes a flat base 12 which is designed to rest upon a floor or the like. In this manner, measuring device 10 is easily portable from location to the other.

Upstanding from base 12 is a brace means 14 against which the sacroiliac of the patient is immovably braced. Brace means 14 includes a pair of vertical supports 16 and a horizontal base bar 18 which is attached to the upper ends of vertical support 16. Suitably attached to a respective vertical support 16 and to base 12 are angled supports 20. Angled supports 20 maintain vertical support 16 and horizontal base bar 18 in position on base 12.

It should be noted that the vertical position of horizontal brace bar 18 is adjustable for different users. This is accomplished by forming each vertical support 16 with an adjusting means 25 having an outer pipe 22 and an inner pipe 24 which is coaxially received an outer pipe 22. As shown in FIG. 1, inner pipe 24 is provided with a plurality of apertures 26 along the length thereof while outer pipe 22 is provided with a single aperture therethrough in which a pin 28 is located. Pin 28 also extends through one of apertures 26 in inner pipe 24 to lock inner pipe 24 at a desired vertical position. By simply removing pin 28, the vertical position of inner pipe 24 and outer pipe 22 is easily adjusted to a desired location.

Attached to horizontal brace bar 18 is a hip holding means 30. Hip holding means 30 is used to hold the hips of the patient in contact with horizontal brace bar 18. Conveniently, hip holding means 30 is an adjustable belt 32 such as typically used for car seat belts or the like. By use of adjustable belt 32, the hips of a user are immovably held in position against horizontal brace bar 18 during use of measuring device 10.

Also attached to vertical support 16 is a knee holding means 34. Knee holding means 34 is used to hold the knees of the patient in a locked position during use of measuring device 10. Conveniently, knee holding means 34 include an adjustable belt 36 similar to adjustable belt 32. The opposite ends of adjustable belt 36 are attached to respective ones of vertical support 16.

Measuring device 10 further includes a foot holding means 40 mounted to base 12. Foot holding means 40 is used to hold the feet of the patient against any upward movement and also to hold the feet directly below the hips during the measurement. Foot holding means 40 includes a pair of wide U shaped mounting members 42 having horizontal portions 44. Mounted for sliding movement along horizontal portions 44 of mounting members 42 is a toe bar 46. Horizontal portions 44 mount toe bar 46 at a height above base 12 such that toe bar 46 is first moved out of the way of the feet of the user as the user initially stands on base 12. Thereafter, after the feet of the user are in position, toe bar 46 is moved along horizontal portions 44 to a position in engagement with the tops of the feet of the user adjacent the toes to hold the feet of the user in place.

Located at approximately the level of and in front of brace bar 18 is a measuring means 50. Measuring means 50 includes a vertical support 52 having an adjusting means 53. Adjusting means 53 includes an inner pipe 54 and an outer pipe 56. Inner pipe 54 includes a plurality of apertures 58. Outer pipe 56 includes a single aperture therethrough in which a pin 60 is received through outer pipe 56 and through appropriate apertures 58 and inner pipe 54. Thus, it can be appreciated that the height of measuring means 50 above base 12 is adjustable by use of adjusting means 53.

Measuring means 50 also includes a platform 62 and a horizontal bar 64 which is suitably mounted by a sliding means 66 to platform 62. Preferably, sliding means 66 is a slot 68 in platform 62 which is covered by a see-through plastic plate 70. Thus, horizontal bar 64 is trapped below plate 70 and is freely slidable in slot 68 in a horizontal direction toward and away from horizontal base bar 18. Plate 70 is suitably attached to platform 62 by screws 72. Provided on plate 70 is a zero point line 74 which extends perpendicular to slot 68 as shown.

In the preferred embodiment of the present invention, horizontal bar 64 includes a rounded tip 76 adjacent horizontal brace bar 18 which is conveniently formed by bending horizontal bar 64 back upon itself. At the other end, horizontal bar 64 includes a handle 78 which is also formed by bending a portion of horizontal bar 64 downwardly from the remaining horizontal portion of horizontal bar 64.

Preferably, measuring means 50 also includes a steel tape measure 80 which is mounted between plate 70 and horizontal bar 64. Tape measure 80 is provided so that the numbered increments thereon face upward and are readable through plate 70. In addition, the clearance between plate 70 and slot 68 is also sufficient to allow tape measure 80 to slide horizontally along the top of horizontal bar 64. Tape measure 80 includes an end catch 82.

Figure 3:
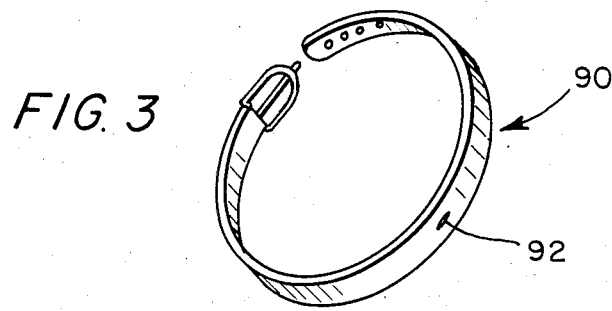
FIG. 3 is a perspective view of an adjustable belt worn by the patient during the measurement.

Depicted in FIG. 3 is an adjustable belt 90 which is preferably worn by the patient. Belt 90 includes a reinforced slot 92. Slot 92 is designed to receive and hold end catch 82 of tape measure 80 therein.

In operation, measuring device 10 functions in the following manner. Initially, horizontal bar 64 and tape measure 80 are pulled back away from horizontal brace bar 18. The patient then steps onto base 12 and positions his hips against horizontal brace bar 18. If necessary, horizontal brace bar 18 is adjusted vertically by adjusting means 25 to the level of the patient's sacroiliac. In addition, the patient's feet are adjusted so as to be directly below the hips of the patient. Once the above position is attained, toe bar 46 of foot holding means 40 is moved along horizontal portions 44 to hold the feet of the patient in position below the hips and also against base 12. After the patient is standing properly on base 12, hip holding means 30 is used to secure the patient's hips against horizontal brace bar 18. This is easily done by suitably hooking adjustable belt 32 together and pulling adjustable belt 32 tight. In the same manner, knee holding means 34 is used to hold the knees of the patient in a locked position by use of adjustable belt 36.

Once the patient is in position, measuring means 50 is suitably adjusted so that the end range extension of the lumbar spine can be measured. In order to accomplish this, horizontal bar 64 and tape measure 80 are advanced toward horizontal brace bar 18 until tip 76 of horizontal bar 64 is immediately adjacent the patient. Platform 62 is then adjusted vertically by adjusting means 53 until tip 76 is immediately opposite a suitable portion of the upper body of the patient, preferably the xiphoid process. After this adjustment, horizontal bar 64 and tape measure 80 are again moved toward the patient until end catch 81 of tape measure 80 and tip 76 of horizontal bar 64 contact the xiphoid process of the patient. At this juncture, adjustable belt 90 is wrapped around the patient so that slot 92 is directly above the xiphoid process. The vertically depending end catch 82 of tape measure 80 is then attached or hooked to belt 90 through reinforced slot 92 in belt 90. At this time, a "zero" reading is made on tape measure 80 by use of zero point line 74.

The patient is next asked to bend back as far as possible. This causes the lumbar spine to bend as far as possible so that end range extension of the lumbar spine can be measured. After the patient has bent back as far as possible, pulling end catch 82 and measure 80 along, a second reading is again made on tape measure 80 at zero-point line 74. It is thus a simple matter to measure the difference between the "zero" reading made of tape measure 80 and the "bent-back" reading subsequently made. The difference between these readings is the end range extension measurement of the lumbar spine for the patient.

It should be appreciated that measuring device 10 is designed to accurately measure the end range extension of the lumbar spine by performing the bending back movement. As the patient bends back, the hips are held stationary against horizontal brace bar 18 so that no hip movement is allowed which might affect the end range measurement. In addition, the knees are kept locked by knee holding means 34 so that any knee movement which might affect the end range measurement is also eliminated. Finally, the feet are held in position by foot holding means 40 so that movement of the feet is also prevented from affecting the measurement. In addition, by use of toe bar 46 of foot holding means 40, there is no danger that the patient might fall backwards over horizontal brace bar 18 as tow bar 46 holds the feet of the patient in contact with base 12.

For best results, it is preferred that a number of end range extension measurements be made for each patient and the results of these measurements averaged. It is expected that this measurement will be made to the nearest ⅛ inch. This measurement should serve as an indication of the amount of end range extension of the lumbar spine and may be used for various diagnostic and preventive care.

Although the use of a separate tape measure 80 has been described for use with measuring device 10, it should be appreciated that it would also be possible to provide measurement increments on horizontal bar 64 itself. In addition, an electronic means for measuring the end range extension of the lumbar spine, such as by a two step movement of horizontal bar 64, would also be possible. Also, it would be possible to adapt presently available electronic rangefinding technology such as used by the photographic industry to make the measurement.

Thus, although the present invention has been described with respect to an exemplary embodiment thereof, it will be understood by those of ordinary skill in the art that variations and modifications can be effected within the scope and spirit of the invention.

I claim:

1. An apparatus for measuring end range extension of a lumbar spine of a standing patient comprising:
    a brace means for immovably bracing the sacroiliac of the patient against backward movement, said brace means terminating adjacent the sacroiliac such that extension of the lumber spine is allowed;
    a hips holding means for holding the hips of the patient in contact with said brace means;
    a foot holding means located adjacent said brace means for holding the feet of the patient against upward movment and directly below the hips; and
    a measuring means located adjacent said brace means for measuring a backward displacement of an identifiable portion of the upper body of the patient.

2. An apparatus as claimed in claim 1 and further including a knee holding means located adjacent said brace means for holding the knees of the patient in a locked position.

3. An apparatus as claimed in claim 2 wherein said measuring means measures the displacement of the xiphoid process of the patient.

4. An apparatus as claimed in claim 2 and further including a base to which said brace means and said foot holding means are attached.

5. An apparatus as claimed in claim 4 wherein said brace means includes a horizontal brace bar, a vertical support, and an adjusting means for adjusting the verticl positon of said horizontal brace bar relative to said vertical support.

6. An apparatus as claimed in claim 5 wherein said knee holding means is attached to said vertical support and said hip holding means is attached to said horizontal brace bar.

7. An apparatus as claimed in claim 6 wherein said hip holding means is an adjustable belt and wherein said knee holding means is an adjustable belt.

8. An apparatus as claimed in claim 4 wherein said measuring means is attached to said base in front of the patient and said brace means, and said measuring means includes a vertical support.

9. An apparatus as claimed in claim 8 wherein said measuring means further includes a horizontal locating bar along which the end range extension is measured, wherein said vertical support includes an adjusting means for adjusting the vertical height of said horizontal locating bar.

10. An apparatus as claimed in claim 9 wherein said vertical support further includes a sliding means for slidably mounting said horizontal locating bar for horizontal sliding movement toward and away from the patient.

11. An apparatus as claimed in claim 10 and further including a measuring tape located adjacent said horizontal locating bar and slidable therealong.

12. An apparatus as claimed in claim 8 wherein said foot holding means is attached to said base and said foot holding means includes a toe bar located above the feet of the user.

13. An apparatus as claimed in claim 12 wherein said foot holding means includes a horizontal support means for adjustably supporting said toe bar slidably therealong.

14. A method for measuring the end range extension of the lumbar spine of a standing patient comprisng the steps of:
    bracing the sacroiliac of the patient against backward movement with a brace while allowing extension of the lumbar spine;
    holding the hips of the patient in contact with the brace;
    holding the feet of the patient against upward movement and directly below the hips; and
    measuring the backward displacement of an identifiable portion of the upper body of the patient as the patient bends as far back as possible from the standing up position.

15. A method for measuring as claimed in claim 14 and further including the step of holding the knees of the patient in a locked position.

16. A method for measuring as claimed in claim 15 wherein said measuring step measures the displacement of the xiphoid process of the patient.

17. A method for measuring as claimed in claim 15 wherein said measuring step includes the measurement of the backwards displacement along a horizontal axis.

* * * * *